(12) United States Patent
Cairns

(10) Patent No.: US 11,865,331 B2
(45) Date of Patent: Jan. 9, 2024

(54) PERIPHERAL NERVE FIELD STIMULATOR CURVED SUBCUTANEOUS INTRODUCER NEEDLE WITH WING ATTACHMENT SPECIFICATION

(71) Applicant: ADVANCED NEUROMODULATION SYSTEMS, INC., Plano, TX (US)

(72) Inventor: Kevin D. Cairns, Fort Lauderdale, FL (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 399 days.

(21) Appl. No.: 16/197,119

(22) Filed: Nov. 20, 2018

(65) Prior Publication Data

US 2019/0083777 A1 Mar. 21, 2019

Related U.S. Application Data

(63) Continuation of application No. 14/858,511, filed on Sep. 18, 2015, now abandoned, which is a continuation of application No. 12/464,470, filed on May 12, 2009, now abandoned.

(60) Provisional application No. 61/052,464, filed on May 12, 2008.

(51) Int. Cl.
*A61N 1/05* (2006.01)
*A61N 1/36* (2006.01)
*A61B 17/34* (2006.01)

(52) U.S. Cl.
CPC ........ *A61N 1/0551* (2013.01); *A61B 17/3468* (2013.01); *A61N 1/36071* (2013.01); *A61B 17/3401* (2013.01)

(58) Field of Classification Search
CPC .............. A61N 1/0551; A61N 1/36071; A61B 17/3468; A61B 17/3401
See application file for complete search history.

(56) References Cited

U.S. PATENT DOCUMENTS

| | | | |
|---|---|---|---|
| 5,250,035 A | 10/1993 | Smith et al. | |
| 5,255,691 A * | 10/1993 | Otten | A61N 1/0551 607/117 |
| 5,489,273 A * | 2/1996 | Whitney | A61M 25/0637 604/160 |

(Continued)

*Primary Examiner* — Kelly J Bekker
*Assistant Examiner* — Andrew P. Restaino
(74) *Attorney, Agent, or Firm* — Norton Rose Fulbright US LLP

(57) ABSTRACT

An apparatus for use in peripheral nerve field stimulation (PNFS) whereby a plurality of curved introducer needles, of varying curvatures, are provided to permit the physician to best locate the region of oligodendrocytes that contain the A Beta fibers by matching the lumbar lordosis. A wing device is also provided that is attachable to the hub of the curved needle introducer which gives the physician better ability to maneuver the needle during insertion as well as permitting tenting of the skin. The invention benefits a large number of painful disorders arising from pathology in the cervical, thoracic, and lumbar spine. In addition, this invention can also help a large number of other conditions including but not limited to failed back surgery syndrome/post-laminectomy pain, occipital/suboccipital headaches, scar pain, post herpetic neuralgia pain, mononeuritis multiplex, and pain following joint surgery (e.g., knee, hip, shoulder).

9 Claims, 8 Drawing Sheets

(56) References Cited

U.S. PATENT DOCUMENTS

| | | | |
|---|---|---|---|
| 6,104,957 A | 8/2000 | Alo et al. | |
| 6,505,075 B1 | 1/2003 | Weiner | |
| 7,302,300 B2 | 11/2007 | Bardy et al. | |
| 7,324,852 B2 | 1/2008 | Barolat et al. | |
| 7,351,196 B2 | 4/2008 | Goldmann et al. | |
| 7,359,755 B2 | 4/2008 | Jones et al. | |
| 2002/0198572 A1* | 12/2002 | Weiner | A61N 1/0504 607/46 |
| 2004/0087970 A1* | 5/2004 | Chu | A61F 2/0045 606/119 |
| 2004/0210245 A1* | 10/2004 | Erickson | A61B 17/3468 606/167 |
| 2005/0090884 A1 | 4/2005 | Honeck | |
| 2005/0240243 A1* | 10/2005 | Barolat | A61N 1/36071 607/46 |
| 2005/0288759 A1* | 12/2005 | Jones | A61B 17/3468 607/116 |
| 2006/0047325 A1 | 3/2006 | Thimineur et al. | |
| 2007/0118196 A1 | 5/2007 | Rooney et al. | |

\* cited by examiner

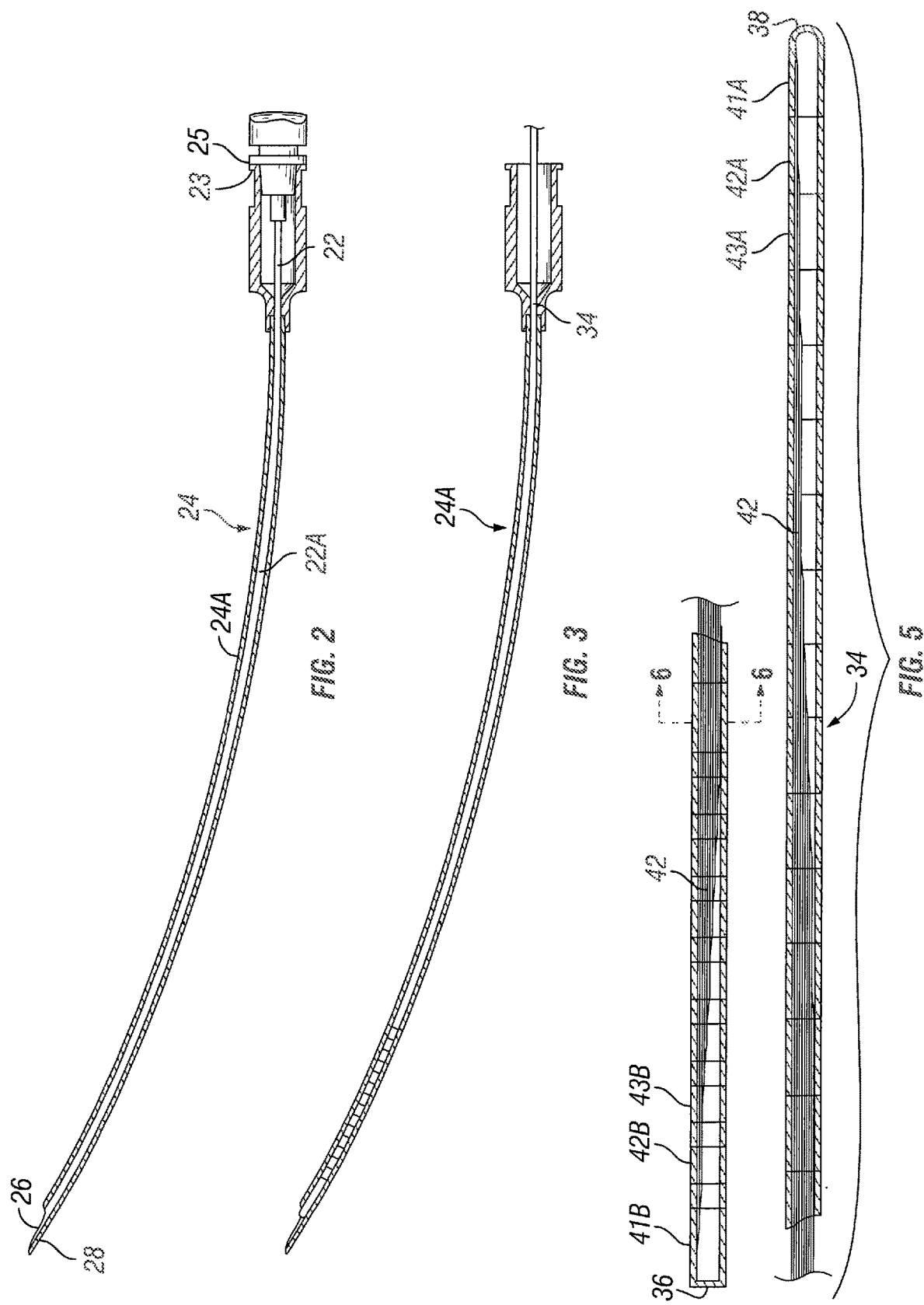

PERIPHERAL NERVE FIELD STIMULATOR CURVED SUBCUTANEOUS INTRODUCER NEEDLE WITH WING ATTACHMENT SPECIFICATION

CROSS-REFERENCE TO RELATED APPLICATIONS

This application is a continuation of U.S. patent application Ser. No. 14/858,511, filed Sep. 18, 2015, which is a continuation of U.S. patent application Ser. No. 12/464,470, filed May 12, 2009, which claims the benefit of U.S. Provisional Application No. 61/052,464, filed May 12, 2008, which is incorporated herein by reference.

FIELD OF INVENTION

The current invention relates to surgical methods, and more particularly, to a neuromodulation device.

BACKGROUND

Peripheral Nerve Field Stimulation (PNFS) is a rapidly growing area of neuromodulation that has shown significant promise in treating patients with cervical, thoracic, and lumbar pain. This procedure, however, has relied on using electrical leads designed for stimulation of the dorsal column of the spinal cord despite the reputed target neural element being a vastly different structure. In peripheral nerve field stimulation, the neural elements that are targeted for depolarization are the terminal dendrocytes located in the subcutaneous region of the patient.

This specific type of neuromodulation is discussed in particular detail in *A Case Report of Subcutaneous Peripheral Nerve Stimulation for the Treatment of Axial Back Pain Associate with Postlaminectomy Syndrome*, by Krutsch, M D, et al., *Neuromodulation: Technology at the Neural Interface*, Vol. 11, Number 2, 2008.

The introducer needle most widely used by peripheral nerve field stimulation implanters is a straight 14 gauge 4½ inch Touhy epidural needle designed for a loss of resistance approach to enter the epidural space rather than placement of electrodes into the subcutaneous region. However, achieving the proper placement of the distal end of the Touhy epidural needle for use during PNFS is very difficult for a number of reasons. The straight needle goes far too deep into the dermis or subcutaneous tissue. In addition, the small surface area of the proximal end of the Touhy epidural needle does not give the physician the required gripping surface area to properly manipulate the distal end of the needle. Furthermore, because of the straight shape of the Touhy needy, the clearance between the needle's proximal end and the physician's fingers with the skin surface make it difficult for the physician to maneuver the needle.

Thus, there remains a need for an apparatus for use in peripheral nerve field stimulation (PNFS) that permits the physician to best locate the region of oligodendrocytes that contain the A Beta nerve fibers for inserting an electrical lead therein.

All references cited herein are incorporated herein by reference in their entireties.

BRIEF SUMMARY

An apparatus for supporting peripheral nerve field stimulation (PNFS) of living being tissue is disclosed. The apparatus comprises: an introducer having a curved portion; a stylet having a curved portion that is similar to the curved portion of the introducer so that the stylet can be inserted within the introducer to form an introducer needle assembly; and wherein the introducer needle assembly provides a passageway through the living being tissue for positioning an electrical lead in a region of oligodendrocytes that contain A Beta fibers when the curved portion of the introducer is passed through the living being tissue and the stylet is removed. In addition, the introducer needle will have a novel "wing-attachment" device that further facilitates the implanting physician to properly position the lead near the A Beta fibers.

A method for positioning an electrical lead within living being tissue to support peripheral nerve field stimulation (PNFS) is disclosed. The method comprises: (a) inserting an introducer needle assembly having a curved portion through the skin of a living being at an entry location displaced away from a target region requiring PNFS; (b) providing a tactile indication of a tip of the curved introducer needle assembly as the tip moves toward the target region, and wherein the target region comprises oligodendrocytes that contain A Beta fibers; (c) tenting the skin at the entry location as the tip is moved toward the target region; (d) removing an insertable portion from the introducer needle assembly; and (e) inserting an electric lead through the introducer needle assembly so that a distal end of the electrical lead is positioned under the target location in preparation for PNFS.

BRIEF DESCRIPTION OF THE SEVERAL VIEWS OF THE DRAWING

The invention will be described in conjunction with the following drawings in which like reference numerals designate like elements and wherein:

FIG. 2 is an enlarged cross-sectional view of the present invention taken along line 2-2 of FIG. 1 and showing the stylet inserted in the introducer;

FIG. 3 is an enlarged cross-sectional view of the present invention taken along line 2-2 of FIG. 1 showing the electrical lead replacing the stylet and inserted within the introducer;

FIG. 5 is an enlarged longitudinal cross-sectional view of the electrical lead taken along line 5-5 of FIG. 1;

DETAILED DESCRIPTION

The invention 20 of the present application of a peripheral nerve field stimulator (PNFS) introducer needle with winged attachment is a useful invention that benefits a large number of painful disorders arising from pathology in the cervical, thoracic, and lumbar spine. In addition, this invention 20 can also help a large number of other conditions including but not limited to failed back surgery syndrome/post-laminectomy pain, occipital/suboccipital headaches, scar pain, post herpetic neuralgia pain, mononeuritis multiplex, and pain following joint surgery (e.g., knee, hip, shoulder).

Figure 1:
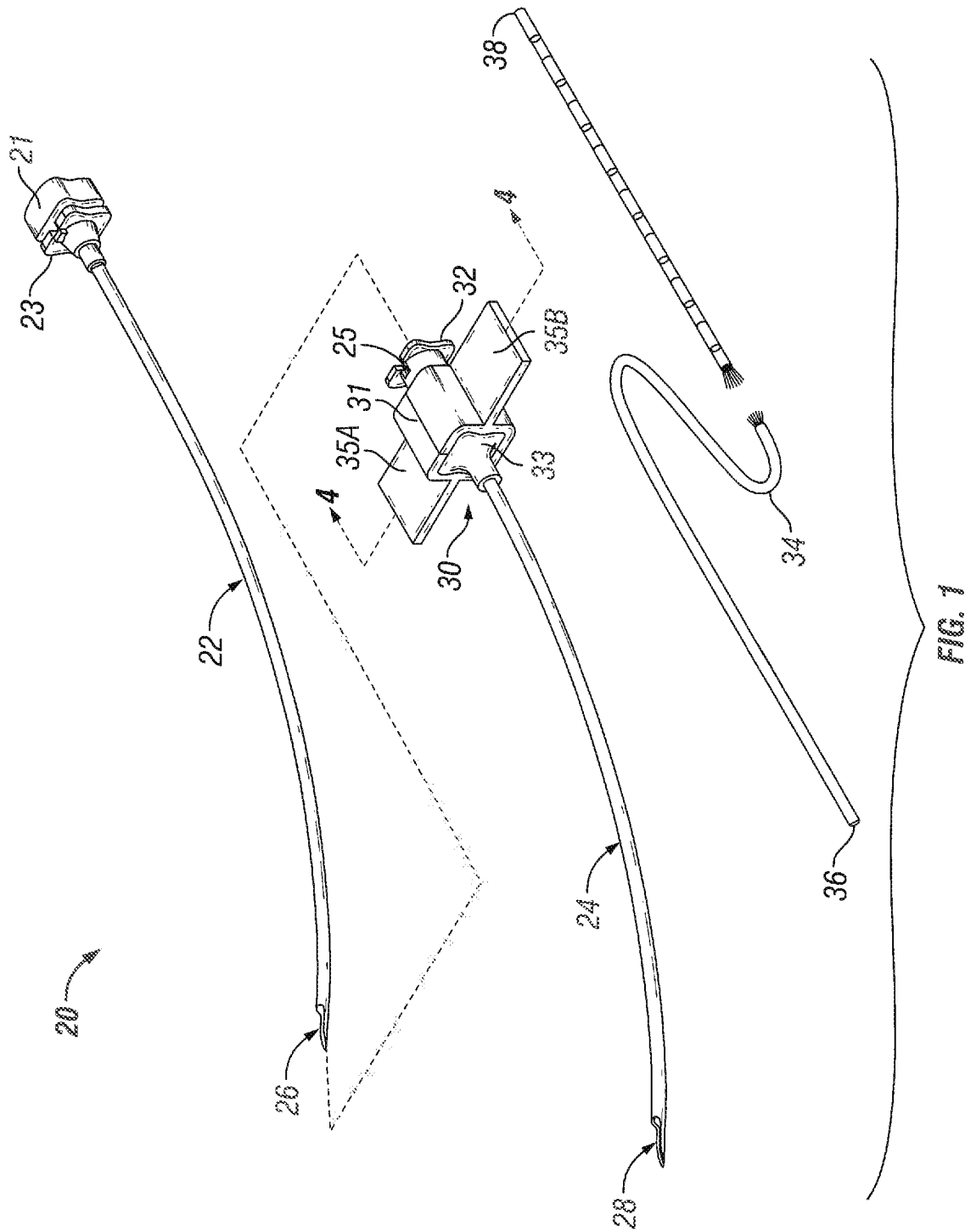
FIG. 1 is an enlarged exploded view of the present invention showing the stylet, the introducer and the electrical lead (also referred to as a "PNFS lead")
Figure 6:
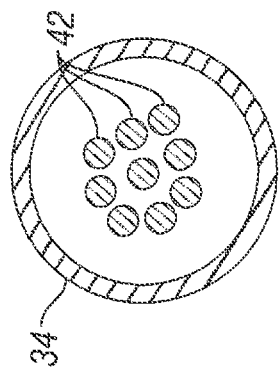
FIG. 6 is an enlarged transverse cross-sectional view of the electrical lead taken along line 6-6 of FIG. 5.
Figure 4:
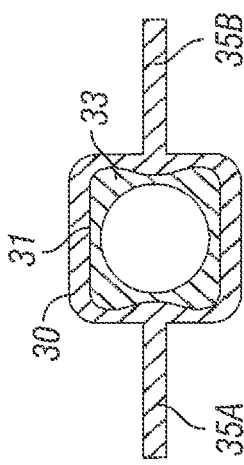
FIG. 4 is an enlarged cross-sectional view of the wing attachment installed on the introducer and taken along line 4-4 of FIG. 1.

In particular, as shown in FIG. 1, the present invention 20 comprises an insert 22 (hereinafter known as a "stylet") that is insertable within a lumen 24 (hereinafter known as an "introducer"). Both of these components comprise beveled flat tips 26 and 28 respectively at their distal ends. The distal tip of the introducer needle could be either sharp or blunt but for illustration purposes is shown as sharp. The distal end 28 of the introducer 24, unlike the stylet 22, is open. When the stylet 22 is inserted into the introducer 24, the present invention forms an introducer needle assembly 20.

Figure 7:
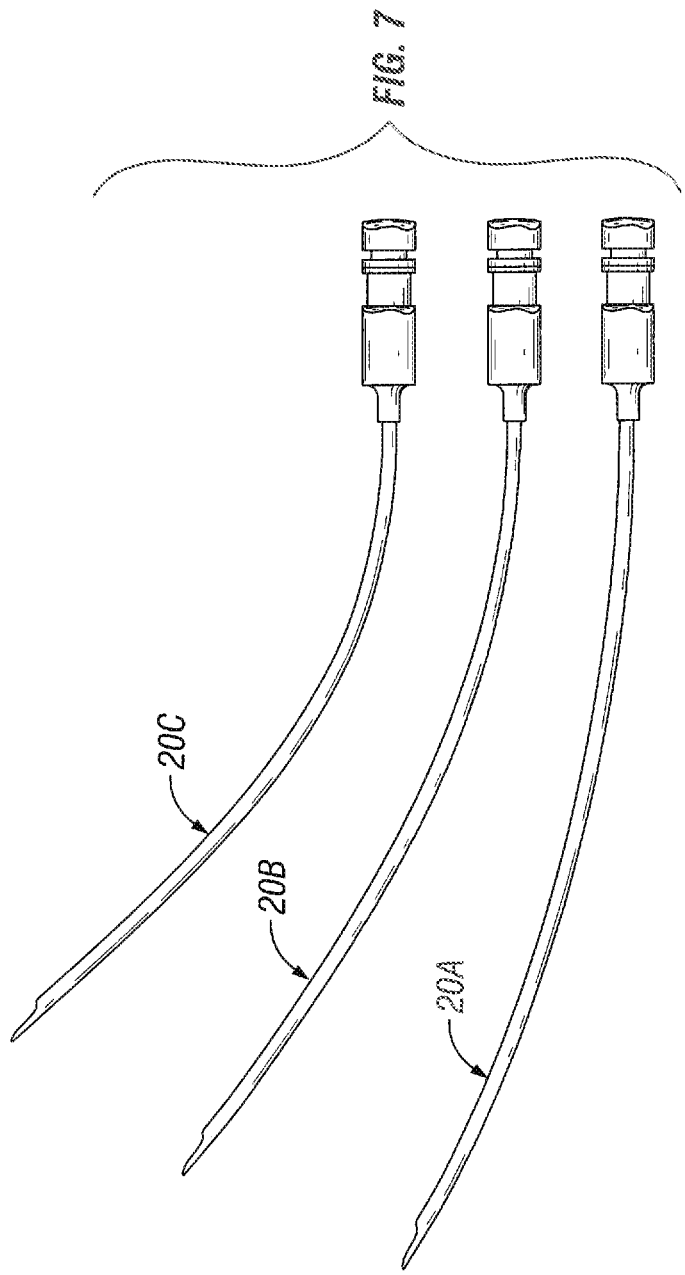
FIG. 7 shows three exemplary embodiments of the present invention having different angles of curvature.

The introducer needle assembly 20 is similar in many ways to a 14 gauge Touhy epidural needle but is unique in its shape. As can be seen in FIGS. 1 and 7, the present invention 20 is curved, having a continuous angle of curvature. By way of example only, some preferred angles of curvature are 15° (see 20A), 25° (20B) and 35° (20C). Both the stylet 22 and the introducer 24 have curved portions 22A and 24B, respectively, as most clearly in shown in FIG. 2, for reasons which will be discussed shortly. Suffice it to say that given that the spine normally has significant lordotic and kyphotic curves, having a curved needle better allows the implanting physician to maintain the same plane in the subdermal region wherein the A Beta fibers lie.

Although the example embodiment has been described in terms of a needle having properties similar to a 14 gauge Touhy needle, those skilled in the art will understand the present invention 20 can include larger and smaller gauge needles, as well as needles with different tips and compositions including but not limited to the Gait Micro Access tear away (model 010-14) and Iflow 17 gauge needle (model #5001376).

Figure 16:
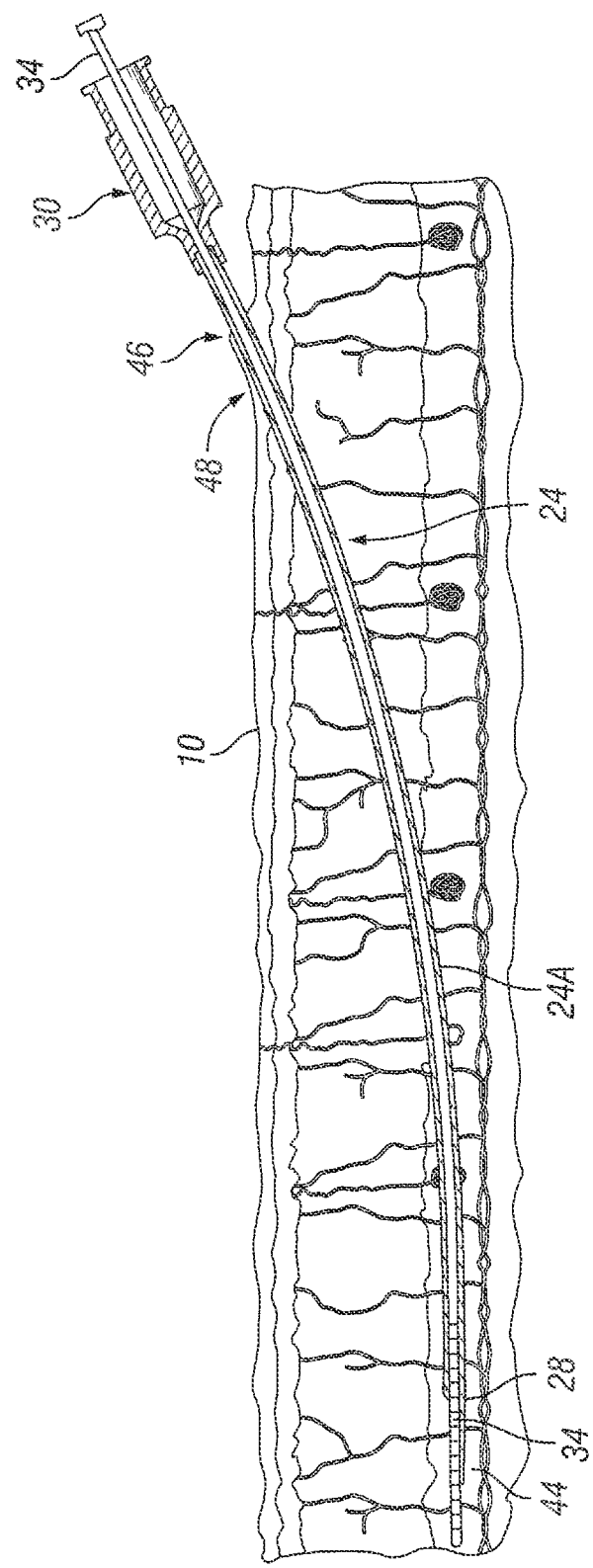
FIG. 16 is a cross-sectional view of the target region showing the insertion of the present invention for properly locating the electrical lead in the region of oligodendrocytes that contain the A Beta fibers.

By way of example only, the length of the introducer needle assembly 20 is approximately 3.5-6 inches. Furthermore, the introducer 24 further comprises an attachable grip 30 at the introducer's proximal end 32. The grip 30 (also referred to as a "wing attachment") permits the physician the ability to more firmly grasp the present invention 20 and to better manipulate it during the PNFS procedure. The wing attachment provides a better gripping and maneuvering surface for the physician implanter to place pressure posteriorly (towards the epidermal layer) once the needle is in the subdermal layer which helps separate the subdermal layer that is rich in A Beta fibers from the dermis and fascial layers (FIG. 16). The grip 30 is severed 31 to permit its releasable attachment to the insertion collar or hub 33 of the introducer 24. For example, to install the grip 30, the grip 30 is slid over the distal end 28 of the introducer 24 and then firmly pushed over the insertion collar or hub 33 until it is positioned as shown in FIG. 1. This makes a snug fit onto the introducer 24. The grip 30 includes a pair of transverse elements or "wings" 35A and 35B that provide the physician with finger grips for precisely manipulating and controlling movement of the introducer needle assembly 20. The winged attachment may be of many different shapes including rectangular, square, circular oblong, and triangular. The wing attachment may be composed of a flexible material such as a plastic polymer, rubber, or malleable metal to further facilitate the implanting physician to grip the introducer and allow for clearance between the introducer and the implanting physicians fingers given that the subdermal layer is often in close approximation to epidermis. The wing attachment may also have a gripping surface such as treads or anti-skid coating material to enable the implanter to better hold the introducer needle. The wing attachment can be attached to the introducer needle in a variety of manners including snapping on, slipping on, clamping on, or clipping on. In addition, the wing device may be attached by other methods including using a glue or tape adhesive material. The wing attachment could even be comprised of a thickened sleeve that would fit around the hub of the Touhy needle. Our description is only one of many ways to attach the wing device for illustration purposes.

It should also be noted that with the grip 30 installed on the hub 33, there is an existing key that permits the physician to "track" the relative position of the curved shaft 24A when inserted into living being tissue. In particular, as shown most clearly in FIG. 1, the stylet 22 includes a hub 21 having a nub 23. When the stylet 22 is property inserted into the introducer 24, the nub 23 fits into a recess 25 in the introducer hub 33. This can also be seen in FIG. 2. When the nub 23 is fitted into the recess 25, the distal end 28 of the introducer 24 points upward, as shown in FIG. 2. Thus, if the physician rotates the introducer 24 about its longitudinal axis, he/she is always aware of which direction the curved distal end 28 is positioned by noting where the nub 23 is positioned.

Figure 14:
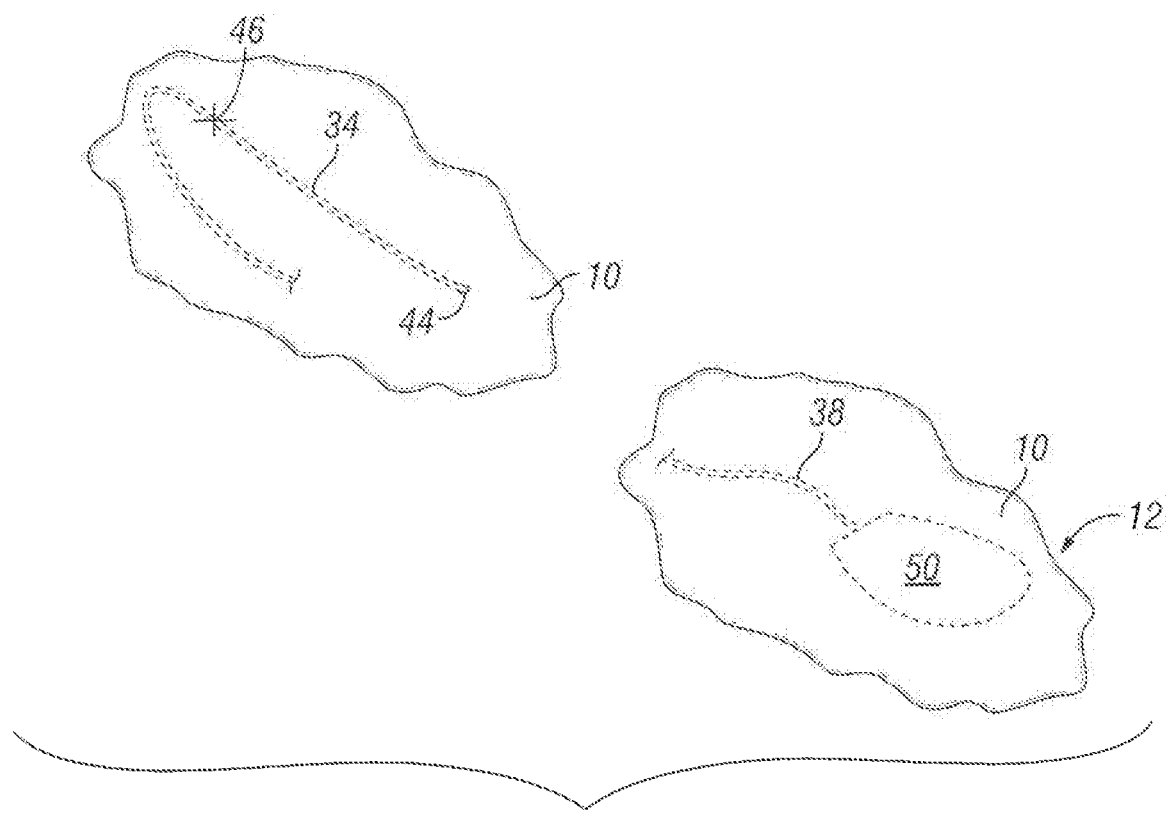
FIG. 14 depicts how the electrical lead is totally embedded in the living being and connected to an embedded power source (e.g., a battery) at another location, e.g., in the buttocks.
Figure 15:
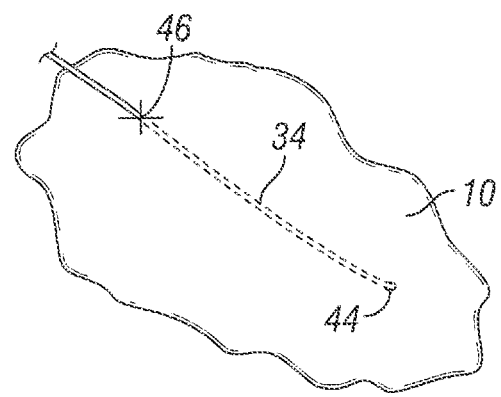
FIG. 15 depicts an alternative application wherein the electrical lead is partially embedded in the living being with a portion emerging from the living being for connection to an external power source (not shown)

As will also be discussed shortly, once the introducer needle assembly 20 is inserted into its proper location in the body, the stylet 22 is removed and an electrical lead (also referred to as a "PNFS lead") 34 is inserted into the introducer 24. Once the distal end 36 of the electrical lead 34 is positioned under the skin 10 at the proper target location, the introducer 24 is removed and the electrical lead 34 is secured to the skin 10. The proximal end 38 of the electrical lead 34 is electrically coupled to a power source, e.g., an external power source (not shown) or to an implanted power source 40 (FIG. 14).

It should be understood that a wide variety of medical leads 34 can be used with the present invention 20 and the invention 20 is not limited to any particular type of medical lead 34. By way of example only, one type of medical lead that can be used with the present invention 20 is an electrical lead such as the Quattrode® #3063 manufactured by Advanced Neuromodulation Systems of Plano, Texas. As can be seen in FIGS. 1 and 5, the electrical lead 34 comprises a plurality of electrode elements that are in electrical communication with respective electrodes via internal conductors 42, as shown by the reference numbers 41A-41B, 42A-42B, 43A-43B, etc. When positioned properly, there may be a 5 cm distance between the most proximal and distal electrode. When energized, localized current passes between corresponding electrode elements and through the closely-adjacent subdermal tissue. However, as mentioned previously, a wide variety of electrical leads 34 can be used with the invention and therefore, the phrase "electrical lead 34" as used throughout this application is meant to include all such types of medical leads and is not limited to that shown in the various figures. For example, another medical lead, such as the Pisces-Octad™ #3788 sold by Medtronic, Inc. of Minneapolis, MN, can also be used.

As can appreciated by those skilled in the art, the stylet 22, while positioned in the introducer 24 when the introducer needle assembly 20 is pushed through the skin layers, the stylet 22 is a solid member that acts to prevent body fluids and tissue from lodging in the introducer 24, thereby preserving the passageway that is formed by the presence of the introducer 24 for eventual displacement by the electrical lead 34.

As mentioned previously, the introducer needle most widely used by peripheral nerve field stimulation implanters is a straight 14 gauge Touhy epidural needle designed for a loss of resistance approach to enter the epidural space rather than placement of electrodes into the subcutaneous region. In PNFS, placement of the electrodes in the electrical lead 34 closest to the target neural elements is best realized by entering the subcutaneous region with the patient in the prone position and "tenting" the needle by placing posterior pressure while advancing to the region of the patient's maximal pain. The placement of posterior pressure once the needle has entered the subdermal layer helps to separate the subdermal layer from the dermis and muscle fascial layer while advancing the needle thereby placing the lead within the layer that contains the highest concentration of A Beta fibers. "Tenting" is a novel technique that enables the implanting physician to more consistently place the electrical lead in the subdermal region. The invention described herein facilitates this novel technique. When done properly, there is minimal resistance and often this layer has an abundance of A Beta fibers allowing maximal stimulation for PNFS which ultimately maximizes pain relief for the patient.

Heretofore, the use of the straight Touhy needle does not affect the proper placement. In contrast, the use of the curved introducer needle assembly 20 permits this proper placement, e.g., the curved portion 22A/24A matches the normal lumbar lordosis present in patients with greater than 90% of patients having a lumbar lordosis of 29-37 degrees off of the sagittal plane.

Figure 8:
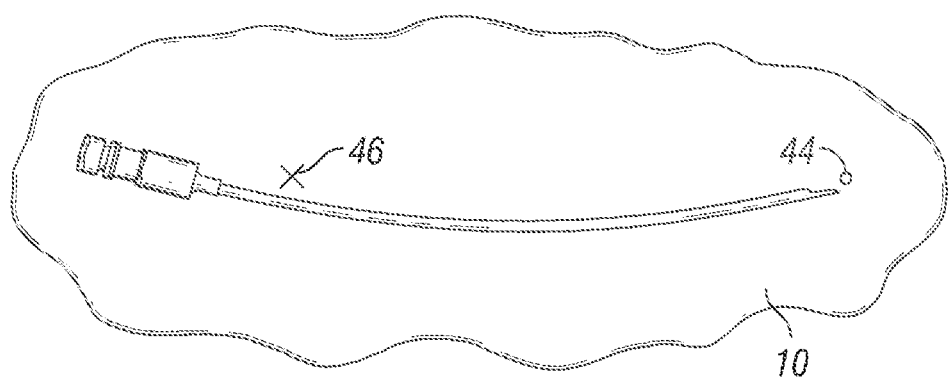
FIG. 8 shows how the present invention is initially used in the PNFS procedure, by marking the area of over the pain on the skin and marking the area for inserting the present invention.
Figure 9:
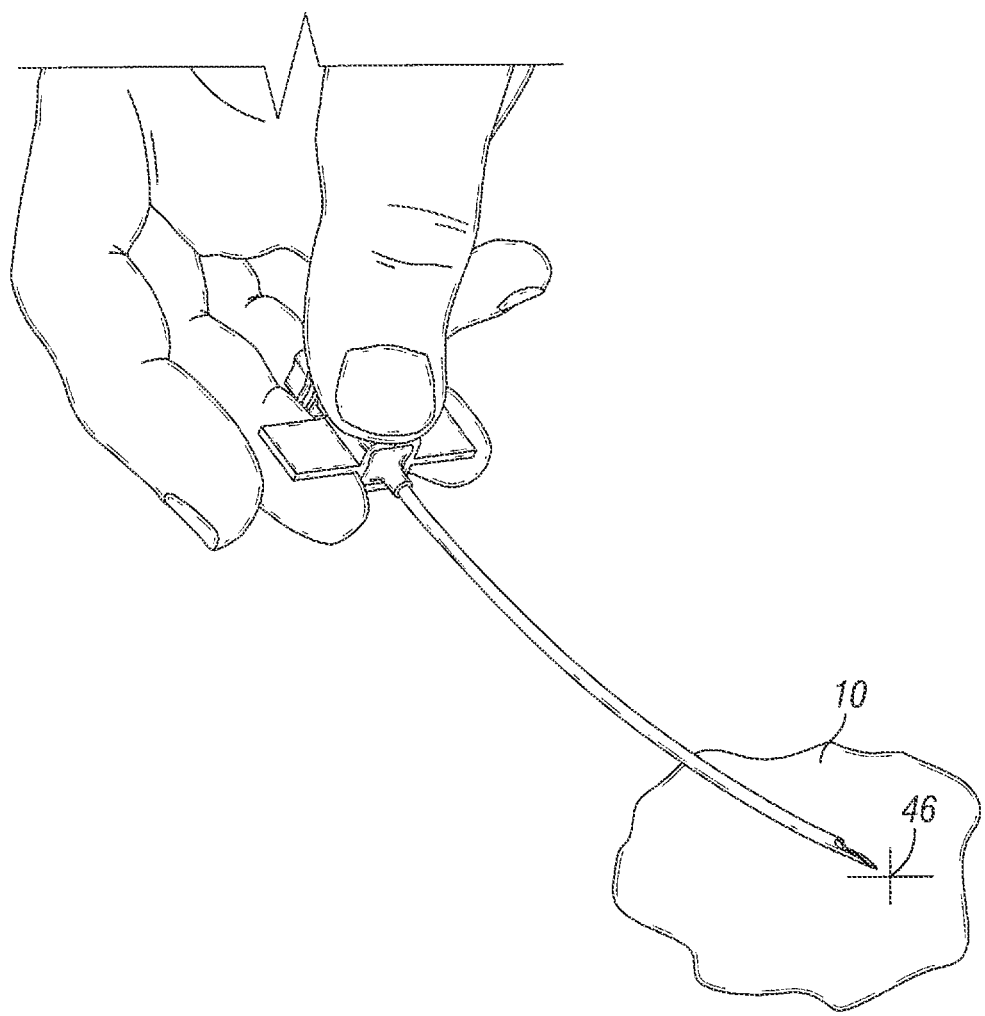
FIG. 9 depicts how the physician grasps the present invention just prior to insertion into the body.

FIGS. 8-14 show an exemplary sequence for achieving positioning the electrical lead 34 using the invention 20 of the present application. With the patient positioned in a prone position, the physician marks on the skin 10 the location under which the electrode distal end 36 ideally needs to be positioned; also referred to as the target location 44 (FIG. 8). At another location on the skin (e.g., 3.5-4.5 inches away from the target location 44), the physician marks the incision point where a small incision is made in the skin. For example, an 11-blade scalpel is used to make a 0.5 cm incision 46. This avoids trauma that would normally occur if the distal end 28 of the introducer needle assembly 20 were simply used to make the initial puncture. With the incision 46, the physician grasps the introducer needle assembly 20 (i.e., the stylet 22 is already inserted therein and the grip 30 has also been previously coupled to the hub 33) as shown in FIG. 9; as can be seen, the physician is able to much more easily manipulate the introducer needle assembly 20 by applying force through his middle and ring fingers on the respective wings 35A/35B thereby "tenting" the skin and separating the dermis from the muscle fascial layer to place the needle in the subdermal region where the A Beta fibers are located.

Figure 10:
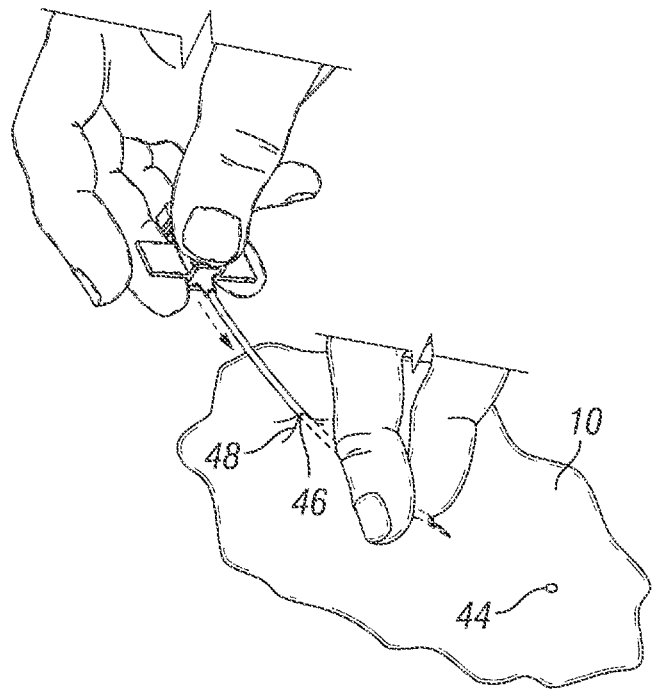
FIG. 10 depicts how the physician "tents" the skin during insertion of the present invention.
Figure 11:
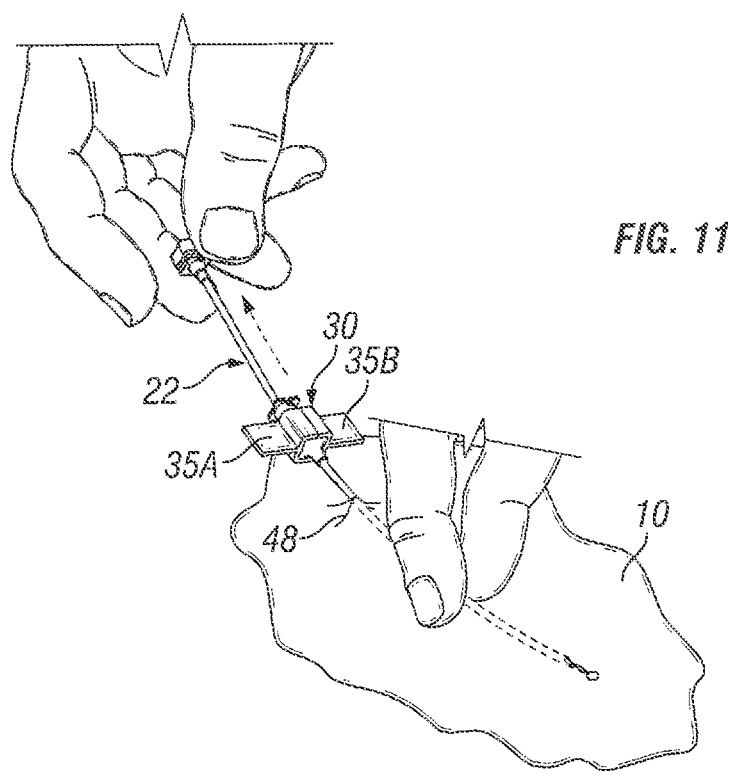
FIG. 11 depicts how the physician guides the proximal end of the present invention under the skin toward the target region.

As the physician continues to insert the introducer needle assembly 20 into the skin 10 towards the target region 44, the curved portion 24A of the introducer rides close to the skin surface, permitting the physician to obtain a tactile indication of the distal end 28 with his/her other hand, as shown in FIG. 10. This has not been possible with the use of the straight Touhy needle. It should also be noted that during this process, the physician is applying a slightly upward force to "tent" the skin (see reference number 48) at the entry location 46. As mentioned earlier, this "tenting" involves placing posterior pressure while advancing to the region of the patient's maximal pain. By tenting and by using his/her other hand to guide the distal end 28 of the introducer needle assembly 20 to the proper subdermal location, the physician prevents the distal end 28 from accidently piercing and exiting the skin 10 or going to deep and entering the muscle tissue. Thus, as mentioned previously, having the attachable grip 30 facilitates the application of posterior pressure and allows for the "tenting" which in turn allows efficient and more reliable placement in the subcutaneous region.

Once the distal end 28 of the introducer needle assembly 20 arrives at the subdermal location beneath the target location 44, the physician removes the stylet 22 (see FIG. 11) from the introducer 24 (without displacing the distal end 28 of the introducer 24 from the subdermal location) while tenting the skin 10 at the incision 46.

Figure 12:
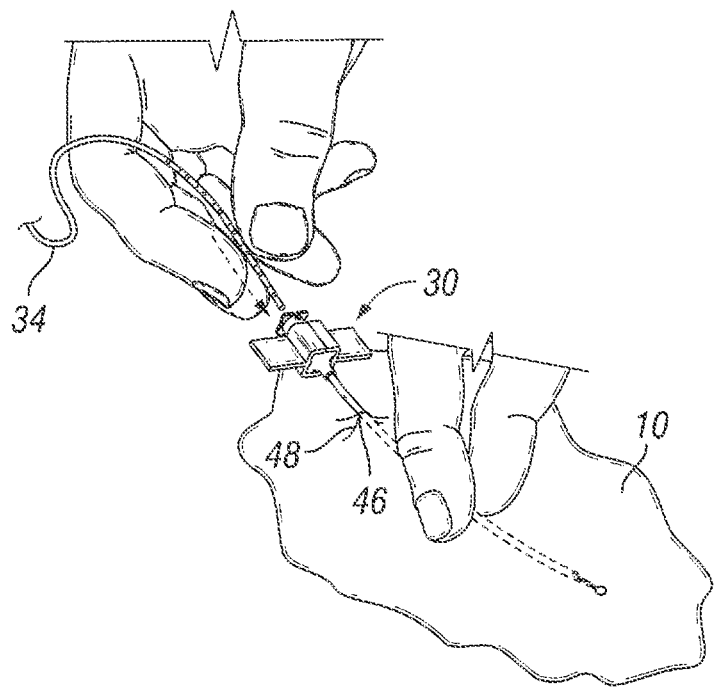
FIG. 12 depicts the present invention, with the stylet removed, and the electrical lead being inserted through the introducer for positioning at the target region.

Next, as shown in FIG. 12, the physician inserts the electrical lead 34 into the introducer 34 until the distal end 36 of the lead 34 is positioned in the desired subdermal location. FIG. 16 depicts how the introducer 24 is oriented for positioning the electrical lead 34 in the region of oligodendrocytes that contain the A Beta fibers.

Figure 13:
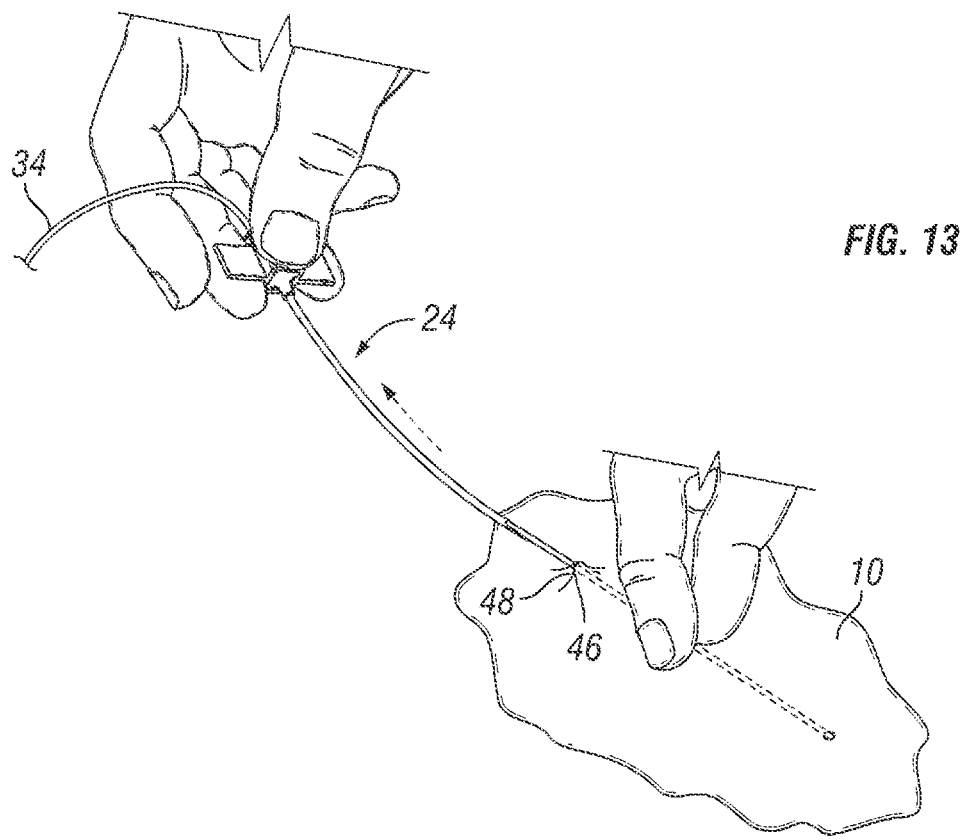
FIG. 13 depicts how the physician removes the introducer once the electrical lead is properly positioned.

While continuing to tent the skin 10, the physician removes the introducer 24, as shown in FIG. 13, leaving the electrical lead 34 in place. The electrical lead 34 is then secured in place (e.g., sutured (not shown), etc.), as shown in FIG. 14. The proximal end 38 of the electrical lead 34 is then electrically connected to an implanted power source, e.g., a rechargeable battery (e.g., 1.5 cm×5 cm×5 cm) that is implanted in, e.g., the buttocks 12 (2 cm deep) to begin the PNFS. Alternatively, a portion of the electrical lead 34, including its proximal end 38, are not embedded in the living being and emerge from the skin 10 to permit the proximal end 38 to be electrically coupled to an external power source (not shown) to begin the PNFS:

By way of example only, kits may be supplied with three different pre-curved needles at approximately 15° (see 20A), 25° (20B) and 35° (20C) angles of curvature. A measuring tape with a marked length (for example, 4.5 inches), to facilitate positioning of the PNFS lead may also be included with the kit. In addition, having markings on the measuring tape to correspond to current lead arrays electrode to electrode distances will better enable to implanting physician to cover the patient's region of pain.

Thus, using the present device and method of the present invention 20, this allows physicians to better introduce the PNFS electrical lead 34 near the oligodendrocytes that contain the A Beta fibers by matching the normal kyphosis and lordosis present throughout the spine, as well as the curvature in the occipital region. In addition, the invention benefits a large number of painful disorders arising from pathology in the cervical, thoracic, and lumbar spine. In addition, this invention can also help a large number of other conditions including but not limited to failed back surgery syndrome/post-laminectomy pain, occipital/suboccipital headaches, scar pain, post herpetic neuralgia pain, mononeuritis multiplex, and pain following joint surgery (e.g., knee, hip, shoulder).

While the invention has been described in detail and with reference to specific examples thereof, it will be apparent to one skilled in the art that various changes and modifications can be made therein without departing from the spirit and scope thereof.

What is claimed:

1. An apparatus for supporting peripheral nerve field stimulation (PNFS) of living being tissue, the apparatus comprising:
    a first introducer having a first curved introducer shaft with a first proximal end and a first distal end, the first curved introducer shaft shaped to have a first curved portion proximate to the first distal end, the first proximal end including an introducer hub;
    a first stylet configured to be inserted within the first introducer to form an introducer needle assembly, the first stylet having a second proximal end and a second distal end, the second proximal end of the first stylet including a stylet hub, the first stylet including a second curved portion having a shape that matches a shape of the first curved portion of the first introducer, wherein:
        the stylet hub includes a nub configured to fit into a recess of the introducer hub to indicate a direction of curvature of the first distal end,
        the first curved portion and the second curved portion are manufactured to have a magnitude of a first angle of curvature of fifteen degrees, twenty five degrees, or thirty five degrees off of a sagittal plane of a patient to facilitate placement of a lead proximate to a subdermal region of a spine of the patient, and
        the first introducer and the first stylet are included in a kit,
        the kit includes a plurality of introducers and a plurality of stylets in addition to the first introducer and the first stylet,
        a second introducer and a second stylet of the plurality of introducers and stylets include, respectively, a third curved portion and a fourth curved portion, each having a second magnitude of a second angle of curvature of fifteen degrees, twenty five degrees, or thirty five degrees off of the sagittal plane of the patient, wherein the second angle of curvature is different from the first angle of curvature,
        the first angle of curvature and the second angle of curvature are selected to facilitate placement of the lead proximate to the subdermal region of the spine of the patient, and
        the subdermal region includes oligodendrocytes that contain A Beta fibers;
    a grip fitted over the introducer hub, the grip severed to permit releasable attachment from the introducer hub;
        the grip including a pair of transverse elements configured to provide for manipulating and controlling movement of the first curved portion proximate to the first distal end of the first introducer;
    the pair of transverse elements configured to facilitate application of posterior pressure sufficient, at the first proximal end, to cause the first curved portion proximate to the first distal end to tent tissue at the first distal end; and
    the first curved introducer shaft including a passageway configured to receive a lead to be positioned proximate to the subdermal region.

2. The apparatus of claim 1, wherein the first introducer provides the passageway through which the lead can be positioned in the subdermal region, and wherein the kit further includes a third introducer and a third stylet of the plurality of introducers and stylets, and wherein the third introducer and the third stylet include, respectively, a fifth curved portion and a sixth curved portion, each having a third magnitude of a third angle of curvature of fifteen degrees, twenty five degrees, or thirty five degrees off of the sagittal plane of the patient, and wherein the third angle of curvature is different from the first and second angle of curvature.

3. The apparatus of claim 1, wherein the first curved introducer shaft is shaped to have a continuous angle of curvature along an entire length thereof between the first proximal and first distal ends.

4. The apparatus of claim 1, wherein the magnitude of the first angle of curvature of the introducer needle assembly coupled with the grip facilitate a tenting procedure of the tissue at the first distal end by reducing a resistance of the tissue to the tenting procedure.

5. The apparatus of claim 1, wherein the grip forms a winged attachment having a circular, oblong, or triangular shape.

6. The apparatus of claim 1, wherein the grip forms a winged attachment composed of a flexible material.

7. The apparatus of claim 1, wherein the first distal end is blunt.

8. A kit for supporting peripheral nerve field stimulation (PNFS) of living being tissue, the kit comprising:
    a plurality of introducers; and
    a plurality of stylets, wherein:
        a first introducer of the plurality of introducers includes a curved introducer shaft with a first proximal end and a first distal end, the curved introducer shaft shaped to have a first curved portion proximate to the first distal end,
        a first stylet of the plurality of stylets is configured to be inserted into the first introducer of the plurality of introducers to form an introducer needle assembly, the first stylet having a second proximal end and a second distal end, the first stylet including a second curved portion having a shape that matches a shape of the first curved portion of the introducer,
        a first angle of curvature of the first curved portion equals a second angle of curvature of the second curved portion, the first angle of curvature and the second angle of curvature being fifteen degrees off of a sagittal plane of a patient,
        a second introducer of the plurality of introducers includes a second curved introducer shaft with a third proximal end and a third distal end, the second curved introducer shaft shaped to have a third curved portion proximate to the third distal end,
        a second stylet of the plurality of stylets is configured to be inserted into the second introducer of the plurality of introducers to form a second introducer needle assembly, the second stylet having a fourth proximal end and a fourth distal end, the second stylet including a fourth curved portion having a shape that matches a shape of the third curved portion of the second curved introducer shaft, and a third angle of curvature of the third curved portion equals a fourth angle of curvature of the fourth curved portion, the third angle of curvature and the fourth angle of curvature being twenty five degrees off of the sagittal plane of a patient.

9. The kit of claim 8, further including a measuring tape with a marked length to facilitate positioning of a PNFS lead.

\* \* \* \* \*